United States Patent [19]

Watanabe et al.

[11] Patent Number: 5,449,803

[45] Date of Patent: Sep. 12, 1995

[54] OXIME ETHER COMPOUND, PROCESSES FOR PREPARING THE SAME AND FUNGICIDE CONTAINING THE SAME

[75] Inventors: Masanori Watanabe; Toshinobu Tanaka; Shuji Yokoyama; Hideaki Umeyama; Tadashi Murakami, all of Ube, Japan

[73] Assignee: UBE Industries, Ltd., Yamaguchi, Japan

[21] Appl. No.: 214,188

[22] Filed: Mar. 17, 1994

[30] Foreign Application Priority Data

Mar. 19, 1993 [JP] Japan .................................. 5-060619

[51] Int. Cl.$^6$ .......................................... C07C 321/10
[52] U.S. Cl. ........................................ 558/1; 564/163; 564/167
[58] Field of Search ................ 564/167; 514/619, 621, 514/624, 530, 531, 539; 560/16; 558/1

[56] References Cited

U.S. PATENT DOCUMENTS

| | | | |
|---|---|---|---|
| Re. 33,989 | 7/1992 | Wenderoth et al. | 514/522 |
| 4,829,085 | 5/1989 | Wenderoth et al. | 514/522 |
| 5,185,342 | 2/1993 | Hayase et al. | 514/274 |
| 5,194,662 | 3/1993 | Brand et al. | 560/35 |

FOREIGN PATENT DOCUMENTS

| | | |
|---|---|---|
| 0299694 | 7/1988 | European Pat. Off. . |
| 0378308 | 1/1990 | European Pat. Off. . |
| 63-23852 | 2/1988 | Japan . |
| 3-246268 | 11/1991 | Japan . |

OTHER PUBLICATIONS

European Search Report completed Dec. 22, 1994 by Examiner H. Kapteyn and mailed Feb. 2, 1995.

Primary Examiner—José G. Dees
Assistant Examiner—Dwayne C. Jones
Attorney, Agent, or Firm—Finnegan, Henderson, Farabow, Garrett & Dunner

[57] ABSTRACT

Disclosed are an oxime ether compound represented by the formula (I):

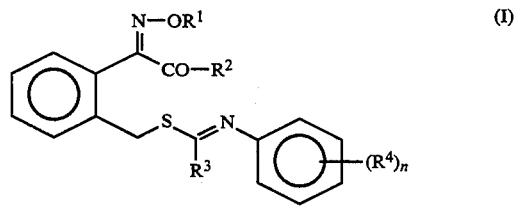

wherein $R^1$ represents an alkyl group having 1 to 6 carbon atoms; $R^2$ represents $OR^5$ or $NHR^6$ where $R^5$ and $R^6$ each represent an alkyl group having 1 to 6 carbon atoms; $R^3$ represents a cycloalkyl group having 3 to 8 carbon atoms; $R^4$ represents an alkenyloxy group having 3 to 6 carbon atoms, an alkynyloxy group having 3 to 6 carbon atoms, an alkoxy group having 1 to 10 carbon atoms, a benzyloxy group, an alkoxycarbonyl group having 2 to 7 carbon atoms, a halogen atom, a cyano group, an alkylthio group having 1 to 6 carbon atoms, an alkyl group having 1 to 6 carbon atoms, a haloalkyl group having 1 to 6 carbon atoms or an acyl group having 2 to 7 carbon atoms; and n represents an integer of 0 to 5.

processes for preparing the same and a fungicide containing the same as an effective ingredient.

7 Claims, No Drawings

OXIME ETHER COMPOUND, PROCESSES FOR PREPARING THE SAME AND FUNGICIDE CONTAINING THE SAME

BACKGROUND OF THE INVENTION

This invention relates to a novel oxime ether type compound useful as a fungicide, processes for preparing the same and a fungicide containing the same as an effective ingredient.

As an oxime ether type compound, there have been known, for example, those as described in Japanese Provisional Patent Publications No. 23852/1988 (which corresponds to U.S. Pat. No. 4,829,085 and U.S. Pat. Re 33,989) and No. 246268/1991 (which corresponds to U.S. Pat. No. 5,185,342). However, the chemical structures of these compounds at the side chain are quite different from that of the present invention and fungicidal activities thereof are also insufficient.

The oxime ether type compound of the present invention and a synthetic intermediate thereof are novel compounds. Thus, it has not been known the oxime ether type compound of the present invention have an excellent fungicidal activity.

SUMMARY OF THE INVENTION

An object of the present invention is to provide a novel oxime ether type compound and a synthetic intermediate thereof, processes for preparing said compounds, and a fungicide containing the novel oxime ether type compound as an effective ingredient.

The present inventors have studied intensively in order to achieve the above object, and consequently found that a novel oxime ether type compound having the following chemical structure has an excellent fungicidal activity as an agricultural and horticultural fungicide and the novel compound can be used as a synthetic intermediate thereof, to accomplish the present invention.

That is, the first invention relates to an oxime ether type compound represented by the formula (I):

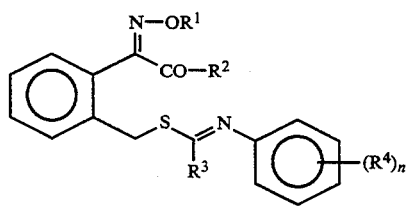

wherein $R^1$ represents an alkyl group having 1 to 6 carbon atoms; $R^2$ represents $OR^5$ or $NHR^6$ where $R^5$ and $R^6$ each represent an alkyl group having 1 to 6 carbon atoms; $R^3$ represents a cycloalkyl group having 3 to 8 carbon atoms; $R^4$ represents an alkenyloxy group having 3 to 6 carbon atoms, an alkynyloxy group having 3 to 6 carbon atoms, an alkoxy group having 1 to 10 carbon atoms, a benzyloxy group, an alkoxycarbonyl group having 2 to 7 carbon atoms, a halogen atom, a cyano group, an alkylthio group having 1 to 6 carbon atoms, an alkyl group having 1 to 6 carbon atoms, a haloalkyl group having 1 to 6 carbon atoms or an acyl group having 2 to 7 carbon atoms; and n represents an integer of 0 to 5.

Geometric isomers (E-isomer and Z-isomer) of the oxime ether portion of the compound (I) of the present invention and a mixture of both isomers are included in the present invention.

The second invention relates to an α-keto ester type compound represented by the formula (II):

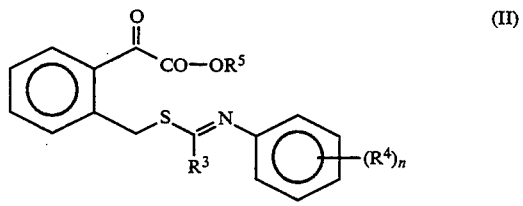

wherein $R^3$, $R^4$, $R^5$ and n have the same meanings as defined above.

The third invention relates to a process for preparing a compound (Ia) wherein $R^2$ in the above formula (I) is $OR^5$, which comprises reacting the compound represented by the above formula (II) with a compound represented by the formula (III):

$$H_2N\text{-}OR^1 \quad (III)$$

wherein $R^1$ has the same meaning as defined above.

The fourth invention relates to a process for preparing a compound (Ib) wherein $R^2$ in the above formula (I) is $NHR^6$, which comprises reacting the compound (Ia) obtained according to the third invention with a compound represented by the formula (IV):

wherein $R^6$ has the same meaning as defined above.

The fifth invention relates to a process for preparing the compound (Ia) wherein $R^2$ in the above formula (I) is $OR^5$, which comprises reacting a compound represented by the formula (V):

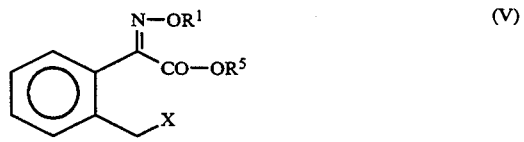

wherein $R^1$ and $R^5$ have the same meanings as defined above; and X represents an eliminatable group, with a compound represented by the formula (VI):

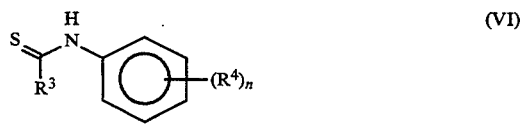

wherein $R^3$ $R^4$ and n have the same meanings as defined above.

The sixth invention relates to a fungicide comprising the compound represented by the above formula (I) as an effective ingredient and a fungicidally effective carrier.

DESCRIPTION OF THE PREFERRED EMBODIMENTS

In the following, the present invention is explained in detail.

In the novel oxime ether type compound (I) which is a desired compound described above, starting compounds (II) to (IV) described above and starting compounds (V) and (VI) described below, $R^1$, $R^2$, $R^3$, $R^4$, $R^5$, $R^6$ and n each have the following meanings.

As $R^1$ there may be mentioned, for example, a straight or branched alkyl group having 1 to 6 carbon atoms, preferably one having 1 to 4 carbon atoms, more preferably a methyl group.

As $R^2$ there may be mentioned $OR^5$ and $NHR^6$.

As $R^5$ or $R^6$ of $R^2$, there may be mentioned, for example, a straight or branched alkyl group having 1 to 6 carbon atoms, preferably those having 1 to 4 carbon atoms, more preferably a methyl group.

As $R^3$ there may be mentioned, for example a cycloalkyl group having 3 to 8 carbon atoms, preferably those having 3 to 4 carbon atoms, more preferably a cyclopropyl group.

As $R^4$ which is a substituent for the phenyl ring other than hydrogen atoms, there may be mentioned an alkenyloxy group having 3 to 6 carbon atoms, an alkynyloxy group having 3 to 6 carbon atoms, an alkoxy group having 1 to 10 carbon atoms, a benzyloxy group, an alkoxycarbonyl group having 2 to 7 carbon atoms, a halogen atom, a cyano group, an alkylthio group having 1 to 6 carbon atoms, an alkyl group having 1 to 6 carbon atoms, a haloalkyl group having 1 to 6 carbon atoms and an acyl group having 2 to 7 carbon atoms.

As the alkenyloxy group having 3 to 6 carbon atoms of $R^4$, there may be mentioned, for example, a straight or branched alkenyloxy group having 3 to 6 carbon atoms, preferably one having 3 or 4 carbon atoms, more preferably an allyloxy group. When $R^4$ is the alkenyloxy group having 3 to 6 carbon atoms, n represents an integer of 0 to 5 and it is preferably 1 or 2, more preferably 1. The substitution position of $R^4$ is not particularly limited, but it is preferably 4-position.

As the alkynyloxy group having 3 to 6 carbon atoms of $R^4$, there may be mentioned, for example, a straight or branched alkynyloxy group having 3 to 6 carbon atoms, preferably one having 3 or 4 carbon atoms, more preferably a propargyloxy group. When $R^4$ is the alkynyloxy group having 3 to 6 carbon atoms, n represents an integer of 0 to 5 and it is preferably 1 or 2, more preferably 1. The substitution position of $R^4$ is not particularly limited, but it is preferably 4-position.

As the alkoxy group having 1 to 10 carbon atoms of $R^4$, there may be mentioned, for example, a straight or branched alkoxy group having 1 to 10 carbon atoms, preferably those having 1 to 4 carbon atoms, more preferably a methoxy group and an ethoxy group. When $R^4$ is the alkoxy group having 1 to 10 carbon atoms, n represents an integer of 0 to 5 and it is preferably 1 or 2. The substitution position of $R^4$ is not particularly limited, but it is preferably 3-, 4- or 5-position.

When $R^4$ is a benzyloxy group, n represents an integer of 0 to 5 and it is preferably 1 or 2, more preferably 1. The substitution position of $R^4$ is not particularly limited, but it is preferably 3- or 4-position.

As the alkoxycarbonyl group having 2 to 7 carbon atoms of $R^4$, there may be mentioned, for example, a straight or branched alkoxycarbonyl group having 2 to 7 carbon atoms, preferably those having 2 to 5 carbon atoms, more preferably a methoxycarbonyl group. When $R^4$ is the alkoxycarbonyl group having 2 to 7 carbon atoms, n represents an integer of 0 to 5 and it is preferably 1 or 2, more preferably 1. The substitution position of $R^4$ is not particularly limited, but it is preferably 4-position.

As the halogen atom of $R^4$, there may be mentioned, for example, a chlorine atom, an iodine atom, a bromine atom and a fluorine atom, preferably a chlorine atom and a fluorine atom. When $R^4$ is a halogen atom, n represents an integer of 0 to 5 and it is preferably 1 or 2, more preferably 1. The substitution position of $R^4$ is not particularly limited, but it is preferably 2-, 3- or 4-position.

When $R^4$ is a cyano group, n represents an integer of 0 to 5 and it is preferably 1 or 2, more preferably 1. The substitution position of $R^4$ is not particularly limited, but it is preferably 4-position.

As the alkylthio group having 1 to 6 carbon atoms of $R^4$, there may be mentioned a straight or branched alkylthio group having 1 to 6 carbon atoms, preferably those having 1 to 4 carbon atoms, more preferably a methylthio group. When $R^4$ is the alkylthio group having 1 to 6 carbon atoms, n represents an integer of 0 to 5 and it is preferably 1 or 2, more preferably 1. The substitution position of $R^4$ is not particularly limited, but it is preferably 3-position.

As the alkyl group having 1 to 6 carbon atoms of $R^4$, there may be mentioned a straight or branched alkyl group having 1 to 6 carbon atoms, preferably those having 1 to 4 carbon atoms, more preferably a methyl group and an ethyl group. When $R^4$ is the alkyl group having 1 to 6 carbon atoms, n represents an integer of 0 to 5 and it is preferably 1 or 2, more preferably 1. The substitution position of $R^4$ is not particularly limited, but it is preferably 3- or 4-position.

As the haloalkyl group having 1 to 6 carbon atoms of $R^4$, there may be mentioned a haloalkyl group having a straight or branched alkyl group having 1 to 6 carbon atoms (as a halogen atom, there may be mentioned those described above, preferably a fluorine atom), preferably those having 1 to 4 carbon atoms, more preferably a trifluoromethyl group. When $R^4$ is the haloalkyl group having 1 to 6 carbon atoms, n represents an integer of 0 to 5 and it is preferably 1 or 2, more preferably 1. The substitution position of $R^4$ is not particularly limited, but it is preferably 4-position.

As the acyl group having 2 to 7 carbon atoms of $R^4$ there may be mentioned a straight or branched acyl group having 2 to 7 carbon atoms, preferably those having 2 to 5 carbon atoms, more preferably an acetyl group. When $R^4$ is the acyl group having 2 to 7 carbon atoms, n represents an integer of 0 to 5 and it is preferably 1 or 2, more preferably 1. The substitution position of $R^4$ is not particularly limited, but it is preferably 4-position.

In the following, Synthetic methods 1 to 3 of the compound (I) of the present invention are described in detail.

Synthetic Method 1

The compound (Ia) wherein $R^2$ in the formula (I) is $OR^5$ can be synthesized by reacting the compound (II) with the compound (III) in a solvent.

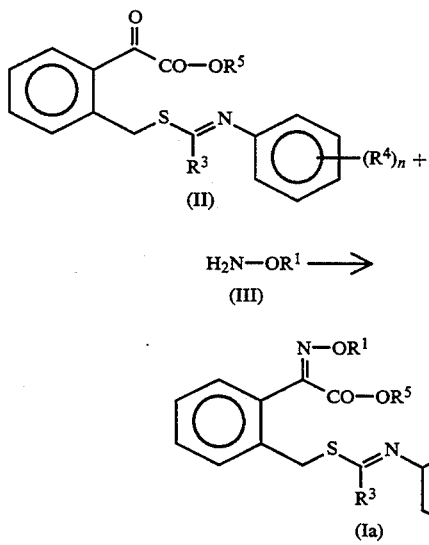

wherein $R^1$, $R^3$, $R^4$, $R^5$ and n have the same meanings as defined above.

The compound (II) and the compound (III) are preferably reacted by using 1 to 50 parts by weight, more preferably 1 to 5 parts by weight of the compound (III) based on 1 part by weight of the compound (II).

The solvent is not particularly limited so long as it does not participate in the present reaction directly and may include, for example, ethers (e.g. diethyl ether, tetrahydrofuran and dioxane), ketones (e.g. acetone and methyl ethyl ketone), alcohols (e.g. methanol, ethanol, n-propanol and isopropanol), amides (e.g. N,N-dimethylformamide and N,N-dimethylacetamide), water and a mixture of the above solvents, preferably a mixture of an alcohol and water.

The amount of the solvent to be used may be such an amount that the concentration of the compound (Ia) becomes 5 to 80% by weight, preferably 10 to 70% by weight.

The reaction temperature is not particularly limited, but it may be in the temperature range of −30° C. to a boiling point or lower of a solvent used, preferably 0° to 50° C.

The reaction time varies depending on the above concentration and temperature, and it may be generally 0.5 to 20 hours, more preferably 1 to 10 hours.

The compound (II) can be prepared by, for example, carrying out the following reaction.

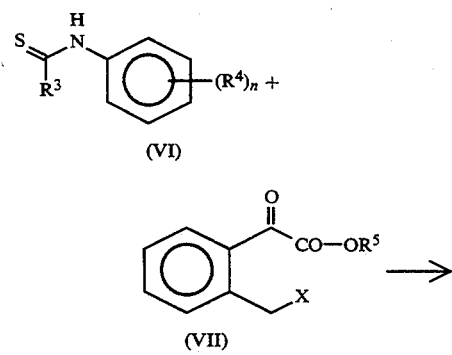

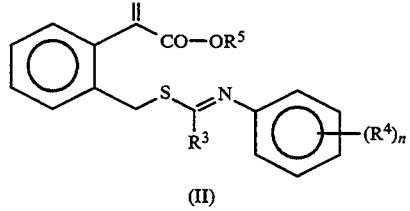

wherein $R^3$, $R^4$, $R^5$ n and X have the same meanings as , , defined above.

The preparation of the compound (II) can be carried out, for example, by dissolving the compound (VI) and the compound (VII) in an organic solvent which does not participate the reaction such as an alcohol having 1 to 10 carbon atoms, a ketone having 3 to 10 carbon atoms, tetrahydrofuran, N, N-dimethylformamide, dimethylsulfoxide and dioxane in the presence of a base such as an alkali metal alkoxide having 1 to 5 carbon atoms, an alkali metal carbonate and an alkali metal hydroxide at a temperature of 0° to 150° C., preferably 30° to 80° C. for 0.5 to 12 hours, preferably 0.5 to 3 hours under stirring. The starting compounds are preferably reacted by using 0.1 to 3 parts by weight, more preferably 0.5 to 1.5 parts by weight of the compound (VII) based on 1 part by weight of the compound (VI).

As X, there may be mentioned, for example, an eliminatable group such as a p-toluenesulfonyloxy group, a methanesulfonyloxy group and a halogen atom, preferably a halogen atom, more preferably a bromine atom.

As the compound (II), there may be mentioned, for example, the compounds (II) comprising the respective substituents corresponding to Compounds (Ia-1) to (Ia-21) in Table 1 shown below (referred to as "Compounds $(II)_{Ia-1}$ to $(II)_{Ia-21}$", for example, Compound $(II)_{Ia-1}$ is the compound represented by the formula (II) in which $R^3$ is a cyclopropyl group, $R^5$ is a methyl group, $R^4$ is a p-allyloxy group and n is 1).

As the compound (III), a commercially available product may be used.

The compound (III) to be used for synthesizing the compound (Ia) of the present invention has an amino group so that an acid addition salt of the compound (III) may be used in place of the compound (III).

As an acid for forming the acid addition salt, there may be mentioned, for example, an inorganic acid (e.g. hydrochloric acid, hydrobromic acid, nitric acid, sulfuric acid and phosphoric acid), a carboxylic acid (e.g. formic acid, oxalic acid, fumaric acid, adipic acid, stearic acid, oleic acid and aconitic acid), an organic sulfonic acid (e.g. methanesulfonic acid, benzenesulfonic acid and p-toluenesulfonic acid) and saccharin.

After completion of the reaction, the desired compound (Ia) prepared as described above may be subjected to conventional post-treatments such as extraction, condensation and filtration, and optionally purified by a known means such as recrystallization and various chromatographic means, if necessary.

As the compound (Ia), there may be mentioned, for example, Compounds (Ia-1) to (Ia-21) in Table 1 shown below (Compound (Ia-1) is the compound represented by the formula (I) in which $R^1$ and $R^5$ are methyl groups, $R^3$ is a cyclopropyl group, $R^4$ is a p-allyloxy group and n is 1).

Synthetic Method 2

The compound (Ib) wherein $R^2$ in the formula (I) is $NHR^6$ can be synthesized generally by reacting the compound (Ia) with the compound (IV) in the presence or absence of a solvent.

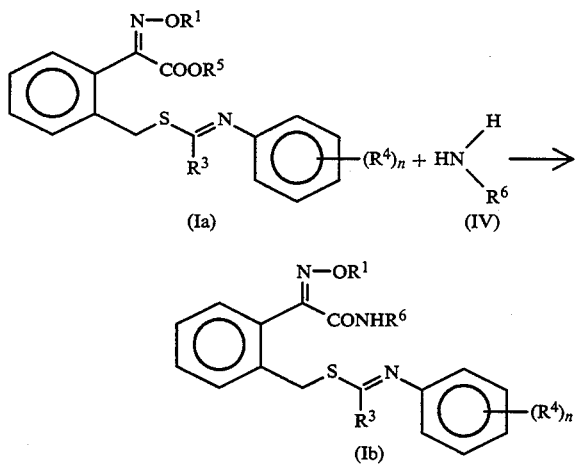

wherein $R^1$, $R^3$, $R^4$, $R^5$, $R^6$ and n have the same meanings as defined above.

The compound (Ia) and the compound (IV) are preferably reacted by using 1 to 50 parts by weight, more preferably 1 to 5 parts by weight of the compound (IV) based on 1 part by weight of the compound (Ia).

As the solvent, there may be mentioned, in addition to the ethers, ketones, alcohols, amides and water described in Synthetic method 1, chlorinated or unchlorinated aromatic, aliphatic or alicyclic hydrocarbons, nitriles (e.g. acetonitrile and propionitrile), organic bases (e.g. triethylamine, pyridine and N,N-dimethylaniline), 1,3-dimethyl-2-imidazolidinone, dimethyl sulfoxide and a mixture of the above solvents.

The amount of the solvent to be used may be such an amount that the concentration of the compound (Ia) becomes 5 to 80% by weight, preferably 10 to 70% by weight.

The reaction temperature is not particularly limited, but it may be in the temperature range of $-30°$ C. to a boiling point or lower of a solvent used, preferably $0°$ to $80°$ C.

The reaction time varies depending on the above concentration and temperature, and it may be generally 0.5 to 40 hours, more preferably 1 to 30 hours.

As the compound (IV), a commercially available product may be used.

The compound (IV) to be used for synthesizing the compound (Ib) of the present invention has an amino group so that an acid addition salt of the compound (IV) may be used in place of the compound (IV).

After completion of the reaction, the desired compound (Ib) prepared as described above may be subjected to conventional post-treatments such as extraction, condensation and filtration, and optionally purified by a known means such as recrystallization and various chromatographic means, if necessary.

As the compound (Ib), there may be mentioned, for example, Compounds (Ib-1) to (Ib-19) in Table 2 shown below (Compound (Ib-1) is the compound represented by the formula (I) in which $R^1$ and $R^6$ are methyl groups, $R^3$ is a cyclopropyl group, $R^4$ is a p-allyloxy group and n is 1).

Synthetic Method 3

The compound (Ia) can be synthesized by reacting the compound (V) with the compound (VI) in the presence or absence of a solvent as shown below. In order to accelerate the reaction, the reaction is preferably carried out in the presence of a base.

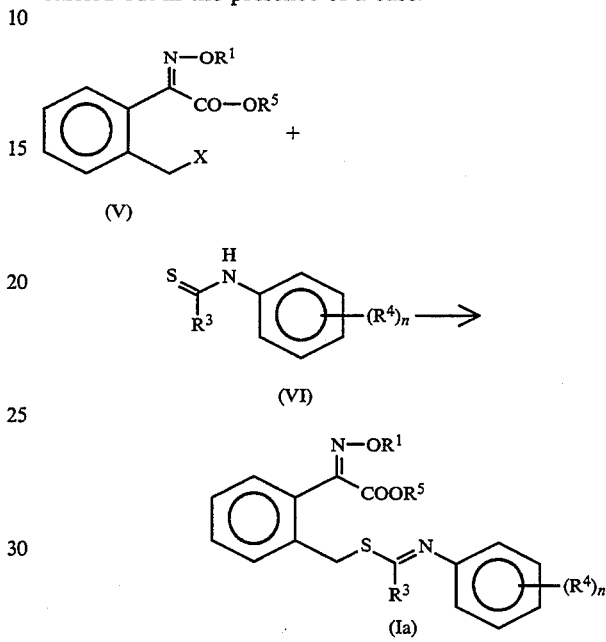

wherein $R^1$, $R^3$, $R^4$, $R^5$, n and X have the same meanings as defined above.

As the solvent, there may be mentioned those described in Synthetic method 2. Among these, an ether solvent such as diethyl ether, tetrahydrofuran and dioxane is particularly preferred.

The amount of the solvent to be used may be such an amount that the concentration of the compound (V) becomes 5 to 80% by weight, preferably 10 to 70% by weight.

The base is not particularly limited and may include, for example, organic bases (e.g. triethylamine, pyridine, N,N-dimethylaniline and 1,8-diazabicyclo[5.4.0]-7-undecene (DBU)), alkali metal alkoxides (e.g. sodium methoxide, sodium ethoxide and potassium-t-butoxide) and inorganic bases (e.g. sodium hydride, sodium amide, sodium hydroxide, potassium hydroxide, sodium carbonate, sodium hydrogen carbonate and potassium carbonate), preferably alkali metal alkoxides.

The amount of the base to be used may be 0.5 to 10-fold mole, preferably 0.8 to 5-fold mole based on the amount of the compound (V).

The reaction temperature is not particularly limited, but it may be in the temperature range of room temperature to a boiling point or lower of a solvent used, preferably $30°$ to $110°$ C.

The reaction time varies depending on the above concentration and temperature, and it may be generally 0.3 to 6 hours, more preferably 0.5 to 4 hours.

The amount of the starting compound (VI) to be used is 0.5 to 2-fold mole, preferably 0.8 to 1.5-fold mole based on the amount of the compound (V).

The compound (V) to be used in the present invention can be prepared by, for example, reacting the compound (VII) and the compound (III) in a solvent as shown below.

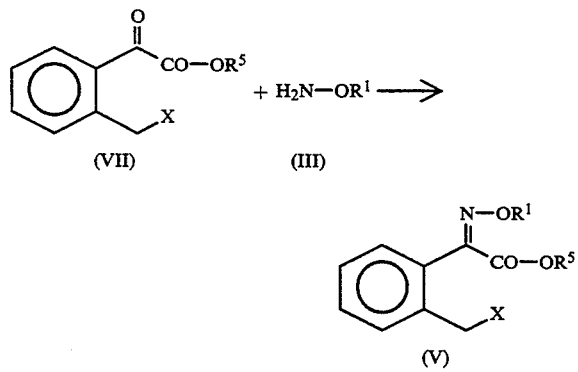

wherein $R^1$, $R^5$ and X have the same meanings as defined above.

As the solvent, there may be mentioned the ethers, alcohols, amides and water described in Synthetic method 1, the hydrocarbons, nitriles, organic bases, 1,3-dimethyl-2-imidazolidinone and dimethyl sulfoxide described in Synthetic method 2 and a mixture of the above solvents.

The amount of the solvent to be used may be such an amount that the concentration of the compound (V) becomes 5 to 80% by weight.

The reaction temperature is not particularly limited, but it may be in the temperature range of room temperature to a boiling point or lower of a solvent used.

The reaction time varies depending on the above concentration and temperature, and it may be generally 2 to 40 hours, more preferably 5 to 30 hours.

The amount of the compound (III) to be used is 0.5 to 3-fold mole, preferably 0.5 to 1.7-fold mole based on the amount of the compound (VII).

After completion of the reaction, the desired compound (V) prepared as described above may be subjected to conventional post-treatments such as extraction, condensation and filtration, and optionally purified by a known means such as recrystallization and various chromatographic means, if necessary.

As the compound (V), there may be mentioned, for example, the compounds (V) comprising the respective substituents corresponding to Compounds (Ia-1) to (Ia-21) in Table 1 shown below (referred to as "Compounds (V)$_{Ia-1}$ to (V)$_{Ia-21}$", geometric isomers (E-isomer and Z-isomer) of the oxime ether portion of the compound (V) are also included, for example, Compound (V)$_{Ia-1}$ is the compound represented by the formula (V) in which $R^1$ and $R^5$ are methyl groups, n is 1, X is a halogen atom and the oxime ether portion is E-configuration).

The compound (VI) can be prepared by, for example, carrying out the following reaction according to the method as described in J. Voss, W. Walter, Ann. 716, 209 (1968).

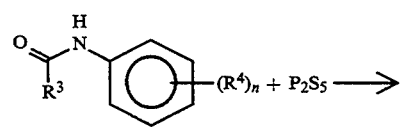

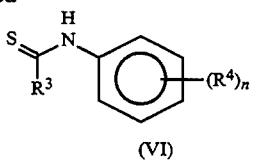

wherein $R^3$, $R^4$ and n have the same meanings as defined above.

As the compound (VI), there may be mentioned, for example, the compounds (VI) comprising the respective substituents corresponding to Compounds (Ia-1) to (Ia-21) in Table 1 shown below (referred to as "Compounds (VI)$_{Ia-1}$ to (VI)$_{Ia-21}$", for example, Compound (VI)$_{Ia-1}$ is the compound represented by the formula (VI) in which $R^3$ is a cyclopropyl group, $R^4$ is a p-allyloxy group and n is 1).

As agricultural and horticultural diseases on which the compound (I) of the present invention exhibits controlling effects, there may be mentioned, for example, brown rust (wheat), powdery mildew (barley), downy mildew (cucumber), blast (rice) and late blight (tomato).

The fungicide of the present invention has a remarkable fungicidal effect and contains at least one compound (I) as an effective ingredient.

The compound (I) can be used singly, but may be preferably used by mixing with a carrier, a surfactant, a dispersant and an auxiliary (for example, prepared as a composition such as a dust, an emulsifiable concentrate, a fine granule, a granule, a wettable powder, an oily suspension and an aerosol) according to a conventional method.

As the carrier, any fungicidally effective carrier may be used, and there may be mentioned, for example, a solid carrier such as talc, bentonire, clay, kaolin, diatomaceous earth, white carbon, vermiculite, calcium hydroxide, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethyl sulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dust, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these Examples.

Reference Example 1

(Synthesis of the Compound (V))

(1) Synthesis of methyl 2-(2'-bromomethylphenyl)-2-methoxyiminoacetate (Compound (V)$_{Ia\text{-}1}$)

In 200 ml of methanol was dissolved 27.7 g of methyl 2-(2'-bromomethylphenyl)-2-oxoacetate, and 1.0 ml of water was added to the solution. Then, 9.10 g of o-methylhydroxylamine hydrochloride was added to the mixture and dissolved while stirring.

After the mixture was stirred at room temperature for one day, the solvent was removed under reduced pressure.

400 ml of ethyl acetate was added to the resulting residue, and the mixture was washed with 200 ml of a saturated saline solution three times and then dried over anhydrous magnesium sulfate.

After drying, the mixture was filtered, and the filtrate was condensed under reduced pressure to obtain a brown oily residue.

The residue was purified by column chromatography (Wako gel C-200 (trade name, manufactured by Wako Junyaku K.K.), eluted with toluene:ethyl acetate changing from 50:1 to 9:1) to obtain 10 g of the title compound (E-isomer) as pale yellow oily liquid which was eluted firstly and then 10 g of the title compound (Z-isomer) as pale yellow oily liquid which was eluted secondly.

(Physical properties of the isomers) .E-isomer $^1$H-NMR (270 MHz, 297 K, CDCl$_3$, TMS) δ: 7.60 to 7.00 (4H, m), 4.34 (2H, s), 4.07 (3H, s), 3.89 (3H, s) ppm .Z-isomer $^1$H-NMR (270 MHz, 297 K, CDCl$_3$, TMS) δ: 7.60 to 7.00 (4H, m), 4.44 (2H, s), 4.06 (3H, s), 3.87 (3H, s) ppm

EXAMPLE 1

(A) Syntheses of the Compounds (II)

(1) Synthesis of methyl 2-{cyclopropyl- (4'-ethoxyphenylimino)methylthiomethyl}phenyloxoacetate (Compounds (II)$_{Ia\text{-}3a}$ and (II)$_{Ia\text{-}3b}$)

100 ml of tetrahydrofuran was added to 5.0 g of methyl 2-(2'-bromomethylphenyl)-2-oxoacetate. Then, 4.3 g of cyclopropylcarbothio-4'-ethoxyanilide was dissolved in the mixture, and while stirring the mixture, 2.6 g of potassium-tert-butoxide was added thereto. The mixture was refluxed under heating for 2 hours.

After completion of the reaction, the reaction mixture was cooled to room temperature, and the solvent was removed by evaporation under reduced pressure.

200 ml of diethyl ether was added to the resulting residue, the mixture was washed with 100 ml of a saturated saline solution three times, and the ether layer was dried over anhydrous magnesium sulfate.

After drying, the ether layer was filtered, and the filtrate was condensed under reduced pressure to obtain a brown oily residue.

The residue was purified by column chromatography (Wako gel C-200 (trade name, manufactured by Wako Junyaku K.K.), eluted by toluene:ethyl acetate=4:1) to obtain 1.2 g of the title compound as pale yellow oily liquid which was eluted firstly.

(Physical properties) $^1$H-NMR (400 MHz, 297 K, CDCl$_3$, TMS) δ: 7.75 to 7.25 (4H, m), 7.00 to 6.65 (4H, m), 4.56 (2H, s), 4.02 (2H, q, 8.0Hz), 3.94 (3H, s), 1.85 to 1.68 (1H, m), 1.43 (3H, t, 8Hz), 1.10 to 0.65 (4H, m) ppm (2) In the same manner as described above, the other compounds (II) corresponding to Compounds (Ia) in Table 1 shown below were synthesized, respectively.

(B) Syntheses of the Compounds (I)

(1) Synthesis of methyl 2-[2'-{cyclopropyl-(4''-ethoxyphenylimino)methylthiomethyl}phenyl]-2-methoxyiminoacetate (Compound (Ia-3a) and Compound (Ia-3b) in Table 1)

After 0.9 g of methyl 2-{cyclopropyl-(4'-ethoxyphenylimino)methylthiomethyl}phenyloxoacetate was dissolved by adding 50 ml of methanol, 3.1 g of potassium carbonate was added to the solution, and the mixture was stirred. To the mixture was added 0.2 g of o-methylhydroxylamine hydrochloride, and the mixture was stirred at room temperature for 4 hours.

After completion of the reaction, the reaction mixture was left to stand overnight and filtered, and then the solvent was removed by evaporation under reduced pressure. To the residue was added 50 ml of diethyl ether, and the mixture was washed with 50 ml of a saturated saline solution three times.

The ether layer was dried over anhydrous magnesium sulfate. Then, the solvent was removed by evaporation under reduced pressure, and the resulting residue was purified by column chromatography (Wako gel C-200 (trade name, manufactured by Wako Junyaku K.K. ), eluted by toluene:ethyl acetate=4:1) to obtain 0.6 g of the title compound as an oily product.

(2) Synthesis of methyl E-2-[2'-{cyclopropyl-(3'',5''-dimethoxyphenylimino)methylthiomethyl}phenyl]-2-methoxyiminoacetate (Compound (Ia-6a) in Table 1)

In 50 ml of tetrahydrofuran was dissolved 1.0 g of cyclopropylcarbothio-3',5'-dimethoxyanilide. Then, 1.2 g of methyl E-2-(2'-bromomethylphenyl)-2-methoxyiminoacetate was added to the solution, and while stirring the mixture, 0.77 g of Potassium-tert-butoxide was added thereto. Then, the mixture was refluxed under heating for 3 hours.

The reaction mixture was condensed under reduced pressure, 100 ml of diethyl ether was added to the residue, and the mixture was washed with 50 ml of a saturated saline solution three times.

The ether layer was dried over anhydrous magnesium sulfate and filtered, and the solvent was removed by evaporation under reduced pressure. The resulting residue was purified by column chromatography (Wako gel C-200 (trade name, manufactured by Wako Junyaku K.K.), eluted with toluene:ethyl acetate changing from 9:1 to 4:1) to obtain 0.62 g of the title compound as an oily product.

(3) Synthesis of methyl 2-[2'-{cyclopropyl-(4"-tolylimino)methylthiomethyl}phenyl]-2-methoxyiminoacetate (Compound (Ia-15) in Table 1)

In 50 ml of tetrahydrofuran was dissolved 0.76 g of cyclopropylcarbothio-4'-methylanilide. Then, 1.14 g of methyl E-2-(2'-bromomethylphenyl)-2-methoxyiminoacetate was added to the solution, and while stirring the mixture, 0.54 g of potassium-tert-butoxide was added thereto. Then, the mixture was refluxed under heating for 3 hours.

After completion of the reaction, the reaction mixture was cooled to room temperature, and the solvent was removed by evaporation under reduced pressure. 100 ml of diethyl ether was added to the residue, and the mixture was washed with 50 ml of a saturated saline solution three times.

The ether layer was dried over anhydrous magnesium sulfate and filtered, and the filtrate was condensed under reduced pressure. The resulting residue was purified by column chromatography (Wako gel C-200 (trade name, manufactured by Wako Junyaku K.K.), eluted by hexane: ethyl acetate=9:1) to obtain 1.05 g of the title compound as an oily product.

(4) Synthesis of N-methyl-2-[2'-{cyclopropyl-(3",5"-dimethoxyphenylimino)methylthiomethyl}phenyl]-2-methoxyiminoacetamide (Compound (Ib-6) in Table 2)

In 20 ml of methanol was dissolved 0.62 g of methyl 2-[2'-{cyclopropyl(3",5"-dimethoxyphenylimino)methylthiomethyl}phenyl]-2-methoxyiminoacetate, and 1.08 g of a 40% methylamine methanol solution was added to the solution. The mixture was stirred at room temperature for one day.

The reaction mixture was condensed under reduced pressure, and the resulting residue was purified by column chromatography (Wako gel C-200 (trade name, manufactured by Wako Junyaku K.K.), eluted with toluene:ethyl acetate changing from 9:1 to 4:1) to obtain 0.4 g of the title compound as an oily product.

(5) Synthesis of N-methyl-2-[2'-{cyclopropyl-(4"-tolylimino)methylthiomethyl}phenyl]-2-methoxyiminoacetamide (Compound (Ib-13) in Table 2)

In 20 ml of methanol was dissolved 0.75 g of methyl 2-[2'-{cyclopropyl(4"-tolylimino)methylthiomethyl}phenyl]-2-methoxyiminoacetate, and 1.50 g of a 40% methylamine methanol solution was added to the solution. The mixture was stirred at room temperature for one day.

The reaction mixture was condensed under reduced pressure, and the resulting residue was purified by column chromatography (Wako gel C-200 (trade name, manufactured by Wako Junyaku K.K.), eluted by toluene:ethyl acetate=9:1) to obtain 0.5 g of the title compound as an oily product.

(6) According to the methods described above, the other compounds (I) in Tables 1 and 2 shown below were synthesized. The compounds ( I ) and physical property values thereof are shown in Tables 1 to 3.

TABLE 1

(Ia)

| Compound | $R^1$ | $R^3$ | Position | $R^4$ | n | $R^5$ | Configuration | Physical properties |
|---|---|---|---|---|---|---|---|---|
| Ia-1 | $CH_3$ |  | 4 | $-OCH_2CH=CH_2$ | 1 | $CH_3$ | E | Data (Ia-1)* |
| Ia-2 | $CH_3$ |  | 4 | $-OCH_2C\equiv CH$ | 1 | $CH_3$ | E | $n_D^{22}$ 1.5885 |
| Ia-3a | $CH_3$ |  | 4 | $-OCH_2CH_3$ | 1 | $CH_3$ | E | Data (Ia-3a)* |
| Ia-3b | $CH_3$ |  | 4 | $-OCH_2CH_3$ | 1 | $CH_3$ | Z | Data (Ia-3b)* |
| Ia-4 | $CH_3$ | 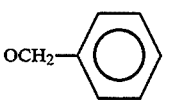 | 4 |  | 1 | $CH_3$ | E | $n_D^{23}$ 1.6006 |
| Ia-5 | $CH_3$ | 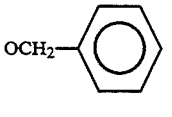 | 3 |  | 1 | $CH_3$ | E | $n_D^{26}$ 1.5720 |
| Ia-6a | $CH_3$ | | 3,5 | both $-OCH_3$ | 2 | $CH_3$ | E | Data (Ia-6a)* |

TABLE 1-continued

(Ia)

| Compound | R¹ | R³ | Position | (R⁴)ₙ R⁴ | n | R⁵ | Configuration | Physical properties |
|---|---|---|---|---|---|---|---|---|
| Ia-6b | CH₃ |  | 3,5 | both —OCH₃ | 2 | CH₃ | Z | Data (Ia-6b)* |
| Ia-7 | CH₃ |  | 4 | —OCOCH₃ | 1 | CH₃ | E | Data (Ia-7)* |
| Ia-8 | CH₃ |  | 2 | —F | 1 | CH₃ | E | $n_D^{26}$ 1.5690 |
| Ia-9 | CH₃ |  | — | — | 0 | CH₃ | E | $n_D^{23}$ 1.5933 |
| Ia-10 | CH₃ |  | 4 | —CN | 1 | CH₃ | E | m.p.: 131 to 132° C. |
| Ia-11 | CH₃ |  | 3 | —SCH₃ | 1 | CH₃ | E | $n_D^{27}$ 1.6032 |
| Ia-12 | CH₃ |  | 3 | —OCH₃ | 1 | CH₃ | E | Data (Ia-12)* |
| Ia-13 | CH₃ |  | 4 | —OCH₃ | 1 | CH₃ | E | Data (Ia-13)* |
| Ia-14 | CH₃ |  | 3 | —CH₃ | 1 | CH₃ | E | Data (Ia-14)* |
| Ia-15 | CH₃ |  | 4 | —CH₃ | 1 | CH₃ | E | Data (Ia-15)* |
| Ia-16 | CH₃ |  | 3 | —CH₂CH₃ | 1 | CH₃ | E | Data (Ia-16)* |
| Ia-17 | CH₃ |  | 4 | —CF₃ | 1 | CH₃ | E | $n_D^{23}$ 1.5759 |
| Ia-18 | CH₃ |  | 3 | —Cl | 1 | CH₃ | E | Data (Ia-18)* |
| Ia-19 | CH₃ |  | 4 | —Cl | 1 | CH₃ | E | Data (Ia-19)* |
| Ia-20 | CH₃ |  | 4 | —COCH₃ | 1 | CH₃ | E | Data (Ia-20)* |
| Ia-21 | CH₃ |  | 4 | —Cl | 1 | CH₃ | E | Data (Ia-21)* |

*Data shown in Table 3.

TABLE 2

(Ib)

[Structure: benzene ring with =N—OR¹ and CONHR⁶ substituents, and —CH₂—S—C(R³)=N—phenyl(R⁴)ₙ]

| Compound | R¹ | R³ | (R⁴)ₙ Position | R⁴ | n | R⁶ | Configuration | Physical properties |
|---|---|---|---|---|---|---|---|---|
| Ib-1 | CH₃ | cyclopropyl | 4 | —OCH₂CH=CH₂ | 1 | CH₃ | E | Data (Ib-1)* |
| Ib-2 | CH₃ | cyclopropyl | 4 | —OCH₂C≡CH | 1 | CH₃ | E | $n_D^{22}$ 1.5892 |
| Ib-3a | CH₃ | cyclopropyl | 4 | —OCH₂CH₃ | 1 | CH₃ | E | Data (Ib-3a)* |
| Ib-3b | CH₃ | cyclopropyl | 4 | —OCH₂CH₃ | 1 | CH₃ | Z | Data (Ib-3b) |
| Ib-4 | CH₃ | cyclopropyl | 4 | —OCH₂—phenyl | 1 | CH₃ | E | $n_D^{23}$ 1.6085 |
| Ib-5 | CH₃ | cyclopropyl | 3 | —OCH₂—phenyl | 1 | CH₃ | E | $n_D^{26}$ 1.5932 |
| Ib-6 | CH₃ | cyclopropyl | 3,5 | both —OCH₃ | 2 | CH₃ | E | Data (Ib-6)* |
| Ib-7 | CH₃ | cyclopropyl | 2 | —F | 1 | CH₃ | E | $n_D^{26}$ 1.5790 |
| Ib-8 | CH₃ | cyclopropyl | — | — | 0 | CH₃ | E | m.p.: 100 to 101° C. |
| Ib-9 | CH₃ | cyclopropyl | 4 | —CN | 1 | CH₃ | E | Data (Ib-9)* |
| Ib-10 | CH₃ | cyclopropyl | 3 | —SCH₃ | 1 | CH₃ | E | $n_D^{27}$ 1.6042 |
| Ib-11a | CH₃ | cyclopropyl | 4 | —OCH₃ | 1 | CH₃ | E | Data (Ib-11a)* |
| Ib-11b | CH₃ | cyclopropyl | 4 | —OCH₃ | 1 | CH₃ | Z | Data (Ib-11b)* |
| Ib-12 | CH₃ | cyclopropyl | 3 | —CH₃ | 1 | CH₃ | E | Data (Ib-12)* |
| Ib-13 | CH₃ | cyclopropyl | 4 | —CH₃ | 1 | CH₃ | E | Data (Ib-13)* |
| Ib-14 | CH₃ | cyclopropyl | 3 | —CH₂CH₃ | 1 | CH₃ | E | Data (Ib-14)* |

TABLE 2-continued (Ib) structure: phenyl ring with N—OR¹ / CONHR⁶ substituent and —S—C(R³)=N—C₆H₄(R⁴)ₙ side chain

| Compound | R¹ | R³ | Position | R⁴ | n | R⁶ | Configuration | Physical properties |
|---|---|---|---|---|---|---|---|---|
| Ib-15 | CH₃ | cyclopropyl | 4 | —CF₃ | 1 | CH₃ | E | Data (Ib-15)* |
| Ib-16 | CH₃ | cyclopropyl | 3 | —Cl | 1 | CH₃ | E | n$_D^{23}$ 1.5669 |
| Ib-17 | CH₃ | cyclopropyl | 4 | —Cl | 1 | CH₃ | E | Data (Ib-17)* |
| Ib-18 | CH₃ | cyclopropyl | 4 | —COCH₃ | 1 | CH₃ | E | Data (Ib-18)* |
| Ib-19 | CH₃ | cyclobutyl | 4 | —Cl | 1 | CH₃ | E | Data (Ib-19)* |

*Data shown in Table 3.

TABLE 3

| Compound | Physical property (¹H-NMR Data) |
|---|---|
| Ia-1 | (CDCl₃, 400MHz) δ: 7.48–7.12(4H, m), 6.89–6.84(2H, m), 6.82–6.77(2H, m), 6.10–6.01(1H, m), 5.44–5.39(1H, m), 5.30–5.25(1H, m), 4.53–4.50(2H, m), 4.09–4.00(5H, m), 3.90–3.70(3H, m), 1.90–1.70(1H, m), 1.20–0.65(4H, m) ppm |
| Ia-3a | (CDCl₃, 200MHz) δ: 7.54–7.05(4H, m), 6.95–6.64(4H, m), 4.20–3.95(7H, m), 3.80(3H, s), 1.90–1.70(1H, m), 1.43–1.30(3H, m), 1.15–0.65(4H, m) ppm |
| Ia-3b | (CDCl₃, 200MHz) δ: 7.64–7.55(1H, m), 7.45–7.20(3H, m), 6.90–6.68(4H, m), 4.50(2H, s), 4.10–3.93(5H, m), 3.85(3H, s), 1.90–1.70(1H, m), 1.45–1.29(3H, m), 1.20–0.65(4H, m) ppm |
| Ia-6a | (CDCl₃, 200MHz) δ: 7.55–7.05(4H, m), 6.18(1H, s), 6.03(2H, s), 4.12(2H, s), 4.08(3H, s), 3.84(3H, s), 3.79(6H, s), 1.90–1.70(1H, m), 1.10–0.65(4H, m) ppm |
| Ia-6b | (CDCl₃, 200MHz) δ: 7.63–7.50(1H, m), 7.45–7.20(3H, m), 6.20(1H, s), 6.03(2H, s), 4.49(2H, s), 4.04(3H, s), 3.84(3H, s), 3.77(6H, s), 1.90–1.73(1H, m), 1.15–0.65(4H, m) ppm |
| Ia-7 | (CDCl₃, 270MHz) δ: 3.55–7.44(1H, d, J=6.5Hz), 7.44–7.25(2H, m), 7.20–7.05(1H, m), 6.90–6.65(4H, m), 4.10(2H, s), 4.04(3H, s), 3.80(3H, s), 1.85–1.65(1H, m), 1.57(3H, s), 1.20–0.60(4H, m) ppm |
| Ia-12 | (CDCl₃, 270MHz) δ: 7.50–7.12(5H, m), 6.63–6.56(1H, m), 6.48–6.38(2H, m), 4.10(2H, brs), 4.05(3H, s), 3.80–3.79(6H, m), 1.70–1.83(1H, m), 1.06–0.91(2H, m), 0.80–0.70(2H, m) ppm |
| Ia-13 | (CDCl₃, 270MHz) δ: 7.60–7.10(4H, m), 6.90–6.70(4H, m), 4.52(2H, s), 4.04(3H, s), 3.88(3H, s), 3.81(3H, s), 1.95–1.75(1H, m), 1.20–0.65(4H, m) ppm |
| Ia-14 | (CDCl₃, 270MHz) δ: 7.55–7.00(5H, m), 6.95–6.75(1H, m), 6.70–6.45(2H, m), 4.14(2H, s), 4.04(3H, s), 3.80(3H, s), 2.34(3H, s), 1.90–1.65(1H, m), 1.20–0.65(4H, m) ppm |
| Ia-15 | (CDCl₃, 200MHz) δ: 7.65–7.05(6H, m), 6.85–6.65(2H, m), 4.20–3.90(5H, m), 3.81(3H, s), 2.32(3H, s), 1.85–1.60(1H, m), 1.15–0.60(4H, m) ppm |
| Ia-16 | (CDCl₃, 270MHz) δ: 7.52–6.73(8H, m), 4.05(3H, brs), 3.88(3H, brs), 3.80(3H, brs), 2.72–2.56(2H, m), 1.80–1.71(1H, m), 1.20–1.28(3H, m), 1.03–0.93(2H, m), 0.80–0.70(2H, m) ppm |
| Ia-18 | (CDCl₃, 270MHz) δ: 7.60–6.50(8H, m), 4.27(2H, s), 4.06(3H, s), 3.85(3H, s), 1.85–1.60(1H, m), 1.15–0.60(4H, m) ppm |
| Ia-19 | (CDCl₃, 270MHz) δ: 7.47–7.12(6H, m), 6.82–6.67(2H, m), 4.09(2H, s), 4.05(3H, s), 3.79(3H, s), 1.75–1.63(1H, m), 1.06–0.92(2H, m), 0.93–0.69(2H, m) ppm |
| Ia-20 | (CDCl₃, 400MHz) δ: 7.94(2H, d, J=8.8Hz), 7.50–7.10(4H, m), 6.90(2H, d, J=8.8Hz), 4.12(2H, s), 4.03(3H, s), 3.80(3H, s), 2.58(3H, s), 1.80–1.60(1H, m), 1.10–0.95(2H, m), 0.85–0.70(2H, m) ppm |
| Ia-21 | (CDCl₃, 270MHz) δ: 7.55–7.05(6H, m), 6.68–6.55(2H, m), 4.05(2H, s), 4.03(3H, s), 3.79(3H, s), 3.50–3.30(1H, m), 2.28–1.30(6H, m) ppm |
| Ib-1 | (CDCl₃, 270MHz) δ: 7.50–7.10(4H, m), 6.92–6.84(2H, m), 6.81–6.66(2H, m), 6.14–5.94(1H, m), 5.41(1H, d, J=16Hz), 5.29(1H, d, J=10.8Hz), 4.55–4.45(2H, m), 4.14–4.06(1H, brs), 4.00–3.85(4H, m), 2.95–2.80(3H, m), 1.85–1.55(1H, m), 1.05–0.95(3H, m), 0.85–0.70(2H, m) ppm |
| Ib-3a | (CDCl₃, 400MHz) δ: 7.50–7.00(5H, m), 6.85–6.60(4H, m), 4.16–4.08(2H, brs), 4.05–3.83(5H, m), 2.95–2.77(3H, m), 1.85–1.70(1H, m), 1.43–1.32(3H, m), 1.15–0.65(4H, m) ppm |
| Ib-3b | (CDCl₃, 400MHz) δ: 7.52–7.08(5H, m), 6.85–6.50(4H, m), 4.60–4.30(2H, m), 4.05–3.85(5H, m), 2.80–2.65(3H, m), 2.05–1.70(1H, m), 1.45–1.30(3H, m), 1.20–0.65(4H, m) ppm |
| Ib-6 | (CDCl₃, 270MHz) δ: 7.55–7.45(1H, m), 7.45–7.25(2H, m), 7.25–7.05(1H, m), 6.77–6.67(1H, brs), 6.18(1H, s), 5.98(2H, s), 4.11(2H, s), 3.95(3H, s), 3.77(6H, s), 2.90–2.80(3H, brs), 1.90–1.70(1H, m), 1.20–0.60(4H, m) ppm |
| Ib-9 | (CDCl₃, 270MHz) δ: 7.60–7.55(4H, m), 7.47–7.43(1H, m), 7.37–7.32(2H, m), 7.15–7.12(1H, m), 6.88–6.84(2H, m), 6.84–6.74(1H, brs), 4.14–4.10(2H, m), 3.94(3H, s), 2.88–2.86(3H, m), 1.70–1.60(1H, m), 1.06–1.01(2H, m), 0.80–0.70(2H, m) |

TABLE 3-continued

| Compound | Physical property ($^1$H-NMR Data) ppm |
|---|---|
| Ib-11a | (CDCl$_3$, 270MHz) δ: 7.60–7.10(4H, m), 6.90–6.55 (5H, m), 4.55–4.35(2H, m), 4.10–3.90(3H, m), 3.80–3.65(3H, m), 2.95–2.60(3H, m), 1.85–1.60 (1H, m), 1.25–0.60(4H, m) ppm |
| Ib-11b | (CDCl$_3$, 400MHz) δ: 7.52–7.10(4H, m), 6.90–6.70 (5H, m), 4.25–4.05(2H, m), 4.00–3.85(3H, m), 3.80–3.75(3H, m), 3.00–2.80(3H, m), 1.80–1.60 (1H, m), 1.20–0.60(4H, m) ppm |
| Ib-12 | (CDCl$_3$, 270MHz) δ: 7.60–7.00(5H, m), 6.90–6.70 (1H, m), 6.70–6.50(3H, m), 4.12(2H, s), 3.96 (3H, s), 2.83–2.79(3H, brs), 2.33(3H, s), 1.80–1.60 (1H, m), 1.20–0.60(4H, m) ppm |
| Ib-13 | (CDCl$_3$, 270MHz) δ: 7.60–7.00(6H, m), 6.85–6.55 (1H, brs), 6.72(2H, d, J=8.1Hz), 4.12(2H, s), 3.96(3H, s), 2.81(3H, d, J=5.1Hz), 2.32(3H, s), 1.85–1.65(1H, m), 1.20–0.60(4H, m) ppm |
| Ib-14 | (CDCl$_3$, 270MHz) δ: 7.52–6.89(6H, m), 6.80–6.57 (3H, m), 4.13(2H, brs), 3.96(3H, brs), 2.40–2.30 (2H, m), 1.72–1.60(1H, m), 1.28–1.18(3H, m), 1.04–0.94(2H, m), 0.78–0.66(2H, m) ppm |
| Ib-15 | (CDCl$_3$, 400MHz) δ: 7.50–6.90(5H, m), 6.85–6.70 (4H, m), 4.13(2H, s), 4.10(3H, s), 2.94(3H, d, J=4.9Hz), 1.80–1.60(1H, m), 1.20–0.65(4H, m) ppm |
| Ib-17 | (CDCl$_3$, 270MHz) δ: 7.49–7.16(6H, m), 6.86–6.70 (3H, m), 4.17(2H, brs), 3.96(3H, brs), 2.85(3H, d, J=2.7Hz), 1.74–1.66(1H, m), 1.07–0.93(2H, m), 0.82–0.73(2H, m) ppm |
| Ib-18 | (CDCl$_3$, 270MHz) δ: 7.92(2H, d, J=6.6Hz), 7.50–7.43 (1H, m), 7.38–7.32(2H, m), 7.17–7.11(1H, m), 6.85(2H, d, J=6.6Hz), 6.73(1H, brs), 4.11 (2H, s), 3.94(3H, s), 2.86(3H, d, J=5.2Hz), 2.57 (3H, s), 1.67–1.47(1H, m), 1.06–0.96(2H, m), 0.80–0.72(2H, m) ppm |
| Ib-19 | (CDCl$_3$, 270MHz) δ: 7.56–6.87(9H, m), 4.20–3.85 (2H, m), 3.86(3H, s), 3.20–2.99(1H, m), 2.97 (3H, d, J=5.1Hz), 2.45–1.70(6H, m) ppm |

EXAMPLE 2

Preparation of Formulations (1) Preparation of granule

Five parts by weight of Compound (Ia-1) was uniformly mixed with 35 parts by weight of bentonite, 57 parts by weight of talc, 1 part by weight of Neopelex powder (trade name, produced by Kao K.K.) and 2 parts by weight of sodium lignosulfonate, and then the mixture was kneaded with addition of a small amount of water, followed by granulation and drying, to obtain a granule.

(2) Preparation of wettable powder

Ten parts by weight of Compound (Ia-1) was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of emulsifiable concentrate

Twenty parts by weight of Compound (Ia-1) was uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dust

Five parts by weight of Compound (Ia-1) was uniformly mixed with 50 parts by weight of talc and 45 parts by weight of kaolin to obtain a dust.

EXAMPLE 3

(Tests of Effects)

(1) Test of controlling effect on downy mildew (cucumber)

In plastic flowerpots having a diameter of 6 cm, one cucumber (variety: Sagami Hanshiro) was grown per one flowerpot, and to the young plants at 1.5 leaf stage, the wettable powders of the desired compounds (I) shown in Tables 1 and 2 prepared as in Example 2 were diluted to a predetermined concentration (200 or 500 ppm) with water containing a surfactant (0.01%), and sprayed in an amount of 20 ml per one flowerpot, respectively.

After spraying, the cucumbers were grown in a glass greenhouse for 2 days, and then zoosporangia of *Pseudoperonospora cubensis* prepared from infected leaves were sprayed uniformly to the back surfaces of the plant leaves to be inoculated thereinto.

After inoculation, the cucumbers were maintained in a dark place at 20° C. for 2 days and then grown in a glass greenhouse for 5 days. The degree of lesion of downy mildew (cucumber) appeared on the first leaves was examined.

As comparative compounds, following Compound A (which corresponds to Compound No. 100 of Japanese Provisional Patent Publication No. 23852/1988) and Compound B (which corresponds to Compound No. 3 of Japanese Provisional Patent Publication No. 246268/1991) are used and tested in the same manner as mentioned above.

Compound A:

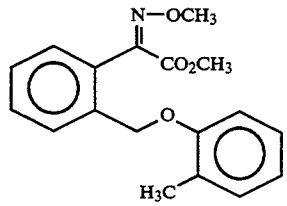

Compound B:

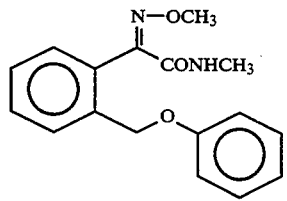

The effect of each chemical was evaluated by using 6 ranks as compared with the degree of lesion in the non-treated district (0: all area is infected, 1: lesion area is about 60% 2: lesion area is about 40% 3:lesion area is about 20% 4: lesion area is 10 % or less and 5: no lesion is observed). The results are shown in Table 4.

TABLE 4

Test of effect on downy mildew (cucumber)

| Treatment concentration: 500 ppm | | Treatment concentration: 200 ppm | |
|---|---|---|---|
| Compound | Effect | Compound | Effect |
| Ia-1 | 5 | Ib-1 | 5 |
| Ia-2 | 5 | Ib-2 | 5 |
| Ia-3a | 5 | Ib-3a | 5 |

TABLE 4-continued

Test of effect on downy mildew (cucumber)

| Treatment concentration: 500 ppm | | Treatment concentration: 200 ppm | |
|---|---|---|---|
| Compound | Effect | Compound | Effect |
| Ia-3b | 4 | Ib-3b | 5 |
| Ia-4 | 5 | Ib-4 | 5 |
| Ia-5 | — | Ib-5 | 4 |
| Ia-6a | 5 | Ib-6 | 5 |
| Ia-6b | 4 | Ib-7 | 5 |
| Ia-7 | 5 | Ib-8 | 5 |
| Ia-8 | 5 | Ib-9 | 5 |
| Ia-9 | 5 | Ib-10 | 5 |
| Ia-10 | 5 | Ib-11a | 5 |
| Ia-11 | 5 | Ib-11b | 5 |
| Ia-12 | 5 | Ib-12 | 5 |
| Ia-13 | 5 | Ib-13 | 5 |
| Ia-14 | 5 | Ib-14 | 5 |
| Ia-15 | 5 | Ib-15 | 5 |
| Ia-16 | 5 | Ib-16 | 5 |
| Ia-17 | 5 | Ib-17 | 5 |
| Ia-18 | 5 | Ib-18 | 4 |
| Ia-19 | 4 | Ib-19 | 5 |
| Ia-20 | 5 | Non-treated district | 0 |
| Ia-21 | 5 | Compound A | 1 |
| | | Compound B | 1 |

(2) Test of controlling effect on blast (rice) (prevention effect)

In plastic flowerpots having a diameter of 6 cm, 10 rices (variety: Nipponbare) were grown per one flowerpot, and to the young plants at 1.5 leaf stage, the wettable powders of the desired compounds (I) shown in Tables 1 and 2 prepared as in Example 2 were diluted to a predetermined concentration (200 or 500 ppm) with water containing a surfactant (0.01%), and sprayed in an amount of 20 ml per one flowerpot, respectively.

After spraying, the rices were grown in a glass greenhouse for 2 days, and then a suspension of conidiospores of *Pyricularia oryzae* was sprayed uniformly to the plant leaves to be inoculated thereinto.

After inoculation, the rices were grown in a greenhouse at 28° C. for 5 days, and the degree of lesion of blast (rice) appeared on the leaves was examined.

The results are shown in Table 5 according to the 6 rank evaluation method described in the above (1).

TABLE 5

Test of effect on blast (rice)

| Treatment concentration: 500 ppm | | Treatment concentration: 200 ppm | |
|---|---|---|---|
| Compound | Effect | Compound | Effect |
| Ia-1 | 5 | Ib-1 | 4 |
| Ia-2 | 4 | Ib-2 | 5 |
| Ia-3a | 4 | Ib-3a | 5 |
| Ia-3b | 4 | Ib-3b | 4 |
| Ia-4 | 4 | Ib-4 | 5 |
| Ia-5 | 4 | Ib-5 | — |
| Ia-6a | 4 | Ib-6 | 5 |
| Ia-6b | — | Ib-7 | 5 |
| Ia-7 | — | Ib-8 | 4 |
| Ia-8 | 4 | Ib-9 | 4 |
| Ia-9 | 5 | Ib-10 | 5 |
| Ia-10 | — | Ib-11a | 5 |
| Ia-11 | — | Ib-11b | — |
| Ia-12 | — | Ib-12 | 5 |
| Ia-13 | 5 | Ib-13 | 4 |
| Ia-14 | 5 | Ib-14 | 4 |
| Ia-15 | 4 | Ib-15 | 5 |
| Ia-16 | 5 | Ib-16 | 5 |
| Ia-17 | 5 | Ib-17 | 5 |
| Ia-18 | 4 | Ib-18 | — |
| Ia-19 | 5 | Ib-19 | 5 |
| Ia-20 | — | Non-treated | 0 |

TABLE 5-continued

Test of effect on blast (rice)

| Treatment concentration: 500 ppm | | Treatment concentration: 200 ppm | |
|---|---|---|---|
| Compound | Effect | Compound | Effect |
| Ia-21 | 5 | district | |
| | | Compound A | 3 |
| | | Compound B | 4 |

(3) Test of controlling effect on powdery mildew (barley) (prevention effect)

In plastic flowerpots having a diameter of 6 cm, 10 barleys (variety: Kuromugi) were grown per one flowerpot, and to the young plants at 1.5 leaf stage, the wettable powders of the desired compounds (I) shown in Tables 1 and 2 prepared as in Example 2 were diluted to a predetermined concentration (200 or 500 ppm) with water containing a surfactant (0.01%), and sprayed in an amount of 20 ml per one flowerpot, respectively.

After spraying, the barleys were grown in a glass greenhouse for 2 days, and then conidiospores of *Erysiphe graminis* were collected from infected leaves and dusted uniformly over the plants to be inoculated thereinto.

After inoculation, the barleys were grown in a glass greenhouse for one week, and the degree of lesion of powdery mildew (barley) appeared on the first leaves was examined.

The results are shown in Table 6 according to the 6 rank evaluation method described in the above (1).

TABLE 6

Test of effect on powdery mildew (barley)

| Treatment concentration: 500 ppm | | Treatment concentration: 200 ppm | |
|---|---|---|---|
| Compound | Effect | Compound | Effect |
| Ia-1 | 5 | Ib-1 | 4 |
| Ia-2 | — | Ib-2 | — |
| Ia-3a | 4 | Ib-3a | 5 |
| Ia-3b | — | Ib-3b | — |
| Ia-4 | — | Ib-4 | — |
| Ia-5 | — | Ib-5 | — |
| Ia-6a | — | Ib-6 | 4 |
| Ia-6b | — | Ib-7 | 5 |
| Ia-7 | 4 | Ib-8 | — |
| Ia-8 | 5 | Ib-9 | 5 |
| Ia-9 | 5 | Ib-10 | — |
| Ia-10 | — | Ib-11a | — |
| Ia-11 | — | Ib-11b | — |
| Ia-12 | 4 | Ib-12 | 5 |
| Ia-13 | 4 | Ib-13 | 4 |
| Ia-14 | 5 | Ib-14 | 4 |
| Ia-15 | 5 | Ib-15 | 5 |
| Ia-16 | 5 | Ib-16 | 5 |
| Ia-17 | 5 | Ib-17 | 5 |
| Ia-18 | 5 | Ib-18 | — |
| Ia-19 | 5 | Ib-19 | 5 |
| Ia-20 | 5 | Non-treated district | 0 |
| Ia-21 | 5 | Compound A | 5 |
| | | Compound B | 5 |

(4) Test of controlling effect on brown rust (wheat) (prevention effect)

In plastic flowerpots having a diameter of 6 cm, 10 wheats (variety: Kobushikomugi) were grown per one flowerpot, and to the young plants at 1.5 leaf stage, the wettable powders of the desired compounds (I) shown in Tables 1 and 2 prepared as in Example 2 to a predetermined concentration (200 or 500 ppm) with water containing a surfactant (0.01%), and sprayed in an amount of 20 ml per one flowerpot, respectively.

After spraying, the wheats were grown in a glass greenhouse for 2 days, and then a suspension of spores of *Puccinia dispersa* ($7 \times 10^4$ spore/ml) was sprayed uniformly to the plants to be inoculated thereinto.

After inoculation, the wheats were grown in a glass greenhouse for one week, and the degree of lesion of brown rust (wheat) appeared on the first leaves was examined.

The results are shown in Table 7 according to the 6 rank evaluation method described in the above (1).

TABLE 7

| Test of effect on brown rust (wheat) | | | |
|---|---|---|---|
| Treatment concentration: 500 ppm | | Treatment concentration: 200 ppm | |
| Compound | Effect | Compound | Effect |
| Ia-1 | 5 | Ib-1 | 5 |
| Ia-2 | 5 | Ib-2 | 4 |
| Ia-3a | 5 | Ib-3a | 5 |
| Ia-3b | 4 | Ib-3b | 5 |
| Ia-4 | 5 | Ib-4 | 5 |
| Ia-5 | 5 | Ib-5 | 4 |
| Ia-6a | 5 | Ib-6 | 5 |
| Ia-6b | 4 | Ib-7 | 5 |
| Ia-7 | 4 | Ib-8 | — |
| Ia-8 | 5 | Ib-9 | 5 |
| Ia-9 | 5 | Ib-10 | — |
| Ia-10 | — | Ib-11a | 5 |
| Ia-11 | 4 | Ib-11b | 5 |
| Ia-12 | 5 | Ib-12 | 5 |
| Ia-13 | 5 | Ib-13 | 5 |
| Ia-14 | 5 | Ib-14 | 5 |
| Ia-15 | 5 | Ib-15 | 5 |
| Ia-16 | 5 | Ib-16 | 5 |
| Ia-17 | 5 | Ib-17 | 5 |
| Ia-18 | 5 | Ib-18 | — |
| Ia-19 | 5 | Ib-19 | 5 |
| Ia-20 | 5 | Non-treated district | 0 |
| Ia-21 | 5 | Compound A | 5 |
|  |  | Compound B | 5 |

(5) Test of chemical damage on cucumber

In plastic flowerpots having a diameter of 6 cm, one cucumber (variety: Sagami Hanshiro) was grown per one flowerpot, and to the young plants at 1.5 leaf stage, the wettable powders of the desired compounds (I) shown in Tables 1 and 2 prepared as in Example 2 were diluted to a predetermined concentration (500 ppm) with water containing a surfactant (0.01%), and sprayed in an amount of 20 ml per one flowerpot, respectively.

After spraying, the cucumbers were grown in a glass greenhouse for 5 days, and then the degree of chemical damages was evaluated.

The results are shown in Table 8.

| Treatment concentration: 500 ppm | |
|---|---|
| Compound | Chemical damage to cucumber |
| Ia-9 | Seldom |
| Compound A | Present |
| Compound B | Present |

As described above, the novel oxime ether type compound of the present invention has an excellent effect as a fungicide without causing any chemical damage to crops.

We claim:

1. An oxime ether compound represented by the formula (I):

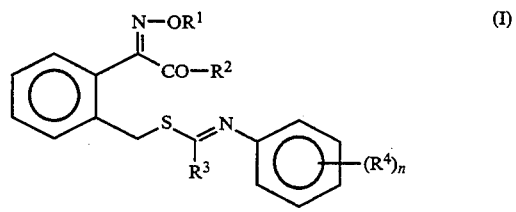

wherein $R^1$ represents an alkyl group having 1 to 6 carbon atoms; $R^2$ represents $OR^5$ or $NHR^6$ where $R^5$ and $R^6$ each represent an alkyl group having 1 to 6 carbon atoms; $R^3$ represents a cycloalkyl group having 3 to 8 carbon atoms; $R^4$ represents an alkenyloxy group having 3 to 6 carbon atoms, an alkynyloxy group having 3 to 6 carbon atoms, an alkoxy group having 1 to 10 carbon atoms, a benzyloxy group, an alkoxycarbonyl group having 2 to 7 carbon atoms, a halogen atom, a cyano group, an alkylthio group having 1 to 6 carbon atoms, an alkyl group having 1 to 6 carbon atoms, a haloalkyl group having 1 to 6 carbon atoms or an acyl group having 2 to 7 carbon atoms; and n represents an integer of 0 to 5.

2. The compound according to claim 1, wherein $R^1$ is an alkyl group having 1 to 4 carbon atoms; $R^2$ is $OR^5$ or $NHR^6$ where $R^5$ and $R^6$ each are an alkyl group having 1 to 4 carbon atoms; $R^3$ is a cycloalkyl group having 3 or 4 carbon atoms; $R^4$ is an alkenyloxy group having 3 or 4 carbon atoms, an alkynyloxy group having 3 or 4 carbon atoms, an alkoxy group having 1 to 4 carbon atoms, a benzyloxy group, an alkoxycarbonyl group having 2 to 5 carbon atoms, a halogen atom, a cyano group, an alkylthio group having 1 to 4 carbon atoms, an alkyl group having 1 to 4 carbon atoms, a haloalkyl group having 1 to 4 carbon atoms or an acyl group having 2 to 5 carbon atoms; and n is an integer of 1 or 2.

3. The compound according to claim 1, wherein the compound is represented by the formula (Ia):

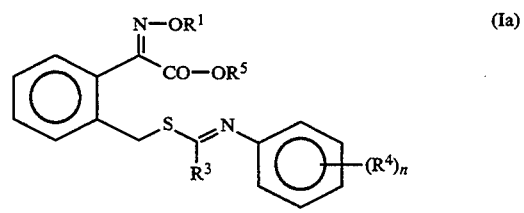

wherein $R^1$, $R^3$, $R^4$, $R^5$ and n have the same meanings as defined in claim 1.

4. The compound according to claim 3, wherein $R^1$ is a methyl group; $R^3$ is a cyclopropyl group; $R^4$ is an allyloxy group, a propargyloxy group, a methoxy group, an ethoxy group, a benzyloxy group, a methoxycarbonyl group, a chlorine atom, a fluorine atom, a cyano group, a methylthio group, a methyl group, an ethyl group, a trifluoromethyl group or an acetyl group; and n is an integer of 1 or 2.

5. The compound according to claim 1, wherein the compound is represented by the formula (Ib):

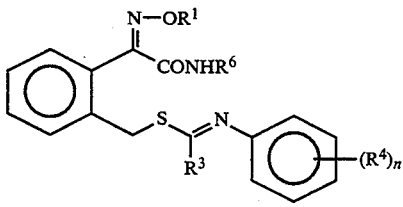

(Ib)

wherein $R^1$, $R^3$, $R^4$, $R^6$ and n have the same meanings as defined in claim 1.

6. The compound according to claim 5, wherein $R^1$ is a methyl group; $R^3$ is a cyclopropyl group; $R^4$ is an allyloxy group, a propargyloxy group, a methoxy group, an ethoxy group, a benzyloxy group, a methoxycarbonyl group, a chlorine atom, a fluorine atom, a cyano group, a methylthio group, a methyl group, an ethyl group, a trifluoromethyl group or an acetyl group; and n is an integer of 1 or 2.

7. A fungicide comprising the compound represented by the formula (I) according to claim 1 as an effective ingredient and a fungicidally effective carrier.

* * * * *